(12) United States Patent
Yasuda et al.

(10) Patent No.: US 9,321,741 B2
(45) Date of Patent: Apr. 26, 2016

(54) COPPER PLATING BATH CONTAINING A TERTIARY AMINE COMPOUND AND USE THEREOF

(75) Inventors: Hiroki Yasuda, Kanagawa (JP); Ryoichi Kimizuka, Tokyo (JP); Tatsuji Takasu, Tokyo (JP); Takuro Sato, Kanagawa (JP); Hiroshi Ishizuka, Kanagawa (JP); Yasuhiro Ogo, Hanoi (VN); Yuto Oyama, Kanagawa (JP); Yu Tonooka, Tokyo (JP); Mikiko Kosaka, Kanagawa (JP); Aya Shimomura, Kanagawa (JP); Yumiko Shimizu, Kanagawa (JP)

(73) Assignee: JCU CORPORATION, Tokyo (JP)

( * ) Notice: Subject to any disclaimer, the term of this patent is extended or adjusted under 35 U.S.C. 154(b) by 659 days.

(21) Appl. No.: 13/695,508

(22) PCT Filed: Apr. 30, 2010

(86) PCT No.: PCT/JP2010/057685
§ 371 (c)(1),
(2), (4) Date: Oct. 31, 2012

(87) PCT Pub. No.: WO2011/135716
PCT Pub. Date: Nov. 3, 2011

(65) Prior Publication Data
US 2013/0043137 A1 Feb. 21, 2013

(51) Int. Cl.
*C25D 3/38* (2006.01)
*C07D 295/08* (2006.01)
(Continued)

(52) U.S. Cl.
CPC .......... *C07D 295/08* (2013.01); *C07D 295/088* (2013.01); *C25D 3/38* (2013.01);
(Continued)

(58) Field of Classification Search
CPC ................................ C25D 3/38; C07D 295/08
See application file for complete search history.

(56) References Cited

U.S. PATENT DOCUMENTS

| 3,329,674 A | 7/1967 | Bulbenko et al. |
|---|---|---|
| 3,369,016 A | 2/1968 | Bulbenko et al. |

(Continued)

FOREIGN PATENT DOCUMENTS

| JP | 53-101380 A | 9/1978 |
|---|---|---|
| JP | 7-159915 A | 6/1995 |

(Continued)

OTHER PUBLICATIONS

International Search Report Issued Jun. 8, 2010 in PCT/JP10/57685 Filed Apr. 30, 2010.

(Continued)

*Primary Examiner* — Keith Hendricks
*Assistant Examiner* — Stefanie S Wittenberg
(74) *Attorney, Agent, or Firm* — Oblon, McClelland, Maier & Neustadt, L.L.P.

(57) ABSTRACT

Provided is a copper plating technique that enables the filling of high aspect-ratio via-holes and through-holes in semiconductor substrates such as silicon substrates, organic material substrates or ceramic substrates. The disclosed technique involves a tertiary amine compound, which is obtained by reacting a heterocyclic compound with the epoxy group of a glycidyl ether group of a compound that has three or more glycidyl ether groups, and a quaternary amine compound thereof, as well as a copper plating additive, a copper plating bath, and a copper plating method employing the compounds.

15 Claims, 1 Drawing Sheet

A

B (51) Int. Cl.
*C07D 295/088* (2006.01)
*H01L 21/768* (2006.01)
*H01L 21/288* (2006.01)
*H05K 3/42* (2006.01)
*H05K 3/46* (2006.01)

(52) U.S. Cl.
CPC ..... *H01L 21/2885* (2013.01); *H01L 21/76898* (2013.01); *H05K 3/423* (2013.01); *H05K 3/421* (2013.01); *H05K 3/4644* (2013.01); *H05K 2201/09509* (2013.01); *H05K 2201/09563* (2013.01)

(56) References Cited

U.S. PATENT DOCUMENTS

| | | | |
|---|---|---|---|
| 3,405,121 A | | 10/1968 | Bulbenko et al. |
| 3,479,337 A | | 11/1969 | Bulbenko et al. |
| 4,253,918 A | * | 3/1981 | Traenckner et al. .......... 522/100 |
| 6,800,188 B2 | * | 10/2004 | Hagiwara ................ C25D 3/38 106/1.26 |
| 7,144,491 B2 | * | 12/2006 | Kumagai ................ C25D 3/38 106/1.26 |
| 7,374,652 B2 | | 5/2008 | Hayashi et al. |
| 8,268,157 B2 | * | 9/2012 | Niazimbetova ...... C07D 233/02 106/1.26 |
| 2003/0106802 A1 | * | 6/2003 | Hagiwara et al. ............. 205/297 |
| 2005/0173256 A1 | | 8/2005 | Kumagai et al. |
| 2007/0007143 A1 | | 1/2007 | Hayashi et al. |
| 2007/0042201 A1 | | 2/2007 | Kumagai et al. |
| 2011/0220513 A1 | * | 9/2011 | Niazimbetova et al. ...... 205/297 |

FOREIGN PATENT DOCUMENTS

| | | |
|---|---|---|
| JP | 2004 137588 | 5/2004 |
| JP | 2007 31834 | 2/2007 |
| JP | 2007-119449 A | 5/2007 |
| WO | 02 090623 | 11/2002 |

OTHER PUBLICATIONS

Combined Office Action and Search Report issued Mar. 13, 2014 in Chinese Patent Application No. 201080066482.0 with English language translation and English translation of categories of cited documents.

Office Action issued Apr. 15, 2014 in Japanese Patent Application No. 2012-512604.

Yang Qing, et al., "Synthesis of Novel Trimeric Surfactant and its property Study", China Academic Journal Electronic Publishing House, vol. 14, No. 20, Oct. 21, 2006, pp. 20-23 with English abstract.

Chen Dan-Dan, et al., "Synthesis and Mixing Properties of Trimeric Cationic Surfactant", China Academic Journal Electronic Publishing House, vol. 24, No. 10, Oct. 2007, pp. 1211-1215 with English abstract.

* cited by examiner

COPPER PLATING BATH CONTAINING A TERTIARY AMINE COMPOUND AND USE THEREOF

This application is a 371 of PCT/JP2010/057685, filed Apr. 30, 2010.

TECHNICAL FIELD

The present invention relates to a novel compound and use thereof, and, more specifically, a tertiary amine compound as a novel compound and a quaternary ammonium compound obtained by quaternerization thereof, as well as a copper plating bath utilizing these novel compounds which is capable of subjecting a semiconductor substrate such as a silicon wafer, or a print circuit board, a substrate having fine circuit patterns or fine pores such as blind via holes, through holes and the like to a copper plating at a high reliability and a copper plating method employing the same.

BACKGROUND ART

Recently, a board laminating process such as a build up process as a circuit mounting of an electronic instrument such as a cell phone, a personal computer, a video instrument, a game machine and the like is brought into an extensive use. This build up process involves a through hole or a via hole provided in a laminate board, and a metal precipitated in such a fine pore serves to establish a connection between the circuit layers thereby enabling a multi-lamination of the circuit. Among such fine pores, the blind via hole is subjected, for the purpose of precipitating a metal therein, to a conformal via hole plating or a via filling plating.

Nevertheless, the via hole plating in which a metal film is formed on the inner wall and the bottom of the via hole involves a difficulty in mounting a conductive layer further on the pore and requires the metal film precipitating area to be increased for ensuring a sufficient current conduction upon establishing a connection between the circuit layers.

On the other hand, a via filling process for filling a via hole with a metal allows a pore to be filled completely, and is extremely advantageous for a down-sizing since another via hole can be formed further on this pore if the surface of the via hole part after the filling is flat. Accordingly, as a substitute for a conformal via hole plating having a limitation in making an insulant (insulating layer) with flat surface, a so-called via filling plating to fill an inter-layer connecting pore (hole) is increasingly brought into use.

As the via filling technology, a copper plating bath containing a condensate of an amine with a glycidyl ether and/or a quaternary ammonium derivative of said condensate has already been known (Patent document 1).

Nevertheless, this technology involved a difficulty in accomplishing a voidless filling of a high-aspect via for a tridimensional mounting such as a blind via hole, a through hole and a through-silicon electrode having a small via diameter to meet a recent demand for structure refinement, although it can readily accomplish the filling of a blind via hole having a large via diameter (10 μm or more) and a relatively small via aspect ratio (via depth/via diameter) (1 or less). A copper plating for LSI can accomplish a filling for up to an aspect ratio of 4 to 5 when the diameter is relatively large (100 nmφ or more) even in a conventional one, but it has a difficulty in accomplishing a satisfactory filling for a recent blind via hole having a smaller diameter.

As a method for precipitating a copper on a print circuit board, the addition of a leveling agent which is a reaction product of a compound selected from imidazoles and the like with an ether bond-containing polyepoxide compound and which has a specific polydispersion degree, into a copper plating bath (Patent document 2).

However, this technology requires the molecular weight distribution to be controlled since the aforementioned reaction product is obtained as being polymerized, resulting in necessity of an enormous effort for accomplishing a consistent production of a leveling agent having an ideal polydispersion degree.

PRIOR ART DOCUMENT

Patent Document

Patent document 1: WO 2002/90623
Patent document 2: U.S. Pat. No. 7,374,652

SUMMARY OF THE INVENTION

Problem to be Solved by the Invention

Accordingly, a copper plating technology allowing a via hole, through hole and the like having a high aspect ratio to be filled has been required for a board such as a silicon board for a semiconductor, an organic material board, and a ceramic board. Also required is a plating fluid technology allowing the blind via hole, through hole and the like to be filled satisfactorily even when the superficial layer plating thickness is reduced for the purpose of achieving a finer circuit.

Means for Solving the Problems

The inventors worked assiduously and found that the aforementioned problem can be solved by utilizing, in a conventional copper plating technology, a novel compound including a tertiary amine compound obtained by reacting a compound having 3 or more glycidyl ether groups with a heterocyclic compound under a gentle condition or a quaternary ammonium compound derived therefrom, thereby establishing the present invention.

Thus, the present invention is as follows.

(1) A tertiary amine compound obtained by reacting a heterocyclic compound with an epoxy group of a glycidyl ether group of a compound having 3 or more glycidyl ether groups.

(2) A quaternary ammonium compound obtained by quaternarizing the tertiary amine compound described in the aforementioned (1).

(3) A method for producing a tertiary amine compound comprising reacting a heterocyclic compound with an epoxy group of a glycidyl ether group of a compound having 3 or more glycidyl ether groups.

(4) A method for producing a quaternary ammonium compound comprising reacting a tertiary amine compound, which is obtained by reacting a heterocyclic compound with an epoxy group of a glycidyl ether group of a compound having 3 or more glycidyl ether groups, with a quaternarizing reagent.

(5) An additive for a copper plating bath comprising one or more compounds selected from the group consisting of the tertiary amine compound described in the aforementioned (1) and the quaternary ammonium compound described in the aforementioned (2).

(6) A copper plating bath comprising one or more compounds selected from the group consisting of the tertiary amine compound described in the aforementioned (1) and the quaternary ammonium compound described in the aforementioned (2).

(7) A copper plating method comprising plating a substrate using a copper plating bath described in the aforementioned (6).

Advantageous Effects of the Invention

A tertiary amine compound and a quaternary ammonium compound obtained by quaternerization thereof according to the present invention, when added to a conventional copper plating bath, allow a semiconductor substrate such as a silicon wafer or a print circuit board, a substrate having fine circuit patterns or fine pores such as blind via holes, through holes and the like to be copper-plated at a high reliability.

In addition, by means of the aforementioned copper plating, a blind via hole, through hole and the like formed at a high aspect ratio on a substrate can be filled with a copper in a void-free manner. At the same time, any overplating of the blind via hole, through hole and the like can be prevented, thereby allowing a superficial layer to be mounted easily and ensuring the flatness of the substrate surface which allows a multilayer to be laminated easily.

Furthermore, the aforementioned copper plating allows for a satisfactory filling performance even with a reduced film thickness of the substrate surface when compared with the copper plating of a substrate using a conventional additive-containing copper plating solution.

DESCRIPTION OF EMBODIMENTS

A novel compound of the present invention is a tertiary amine compound (hereinafter referred to as "a tertiary compound of the invention") obtained by reacting a compound having 3 or more glycidyl ether groups with a heterocyclic compound via a reaction at the epoxy group of the glycidyl ether group.

The compound having 3 or more glycidyl ether groups serving as a starting material for the aforementioned tertiary compound of the invention is not limited particularly and may for example be a compound represented by Formula (I) shown below (hereinafter referred to simply as "Compound (I)").

wherein:

$R^1$ is a hydrogen atom, a formyl group or one or two glycidyl ether groups optionally containing a carbonyl group constituted by $C_4$-$C_8$ and $C_2$-$C_4$, preferably a hydrogen atom or a glycidyl ether group;

$R^2$ is a hydrogen atom, a methyl group or an ethyl group, preferably a hydrogen atom or an ethyl group;

$R^3$ is a hydrogen atom, a formyl group or one or two glycidyl ether groups optionally containing a carbonyl group constituted by $C_4$-$C_8$ and $O_2$-$O_4$, preferably a hydrogen atom or a glycidyl ether group; and, n is an integer of 1 to 4.

Typically, the aforementioned compound (I) may for example be those listed below. These compounds (I) are commercially available or can be obtained by those skilled in the art by reacting a polyol corresponding to a compound having 3 or more glycidyl ether groups with epichlorohydrin according to Chemical Abstract (vol. 73, 57454n. (1970)).

TABLE 1

| Compound | n | $R^1$ | $R^2$ | $R^3$ |
|---|---|---|---|---|
| Glycerin triglycidyl ether | 1 | H | H | H |
| Trimethylolpropane triglycidyl ether | 1 | H | —$CH_2CH_3$ | H |
| Diglycerol tetraglycidyl ether | 2 | H | H | H |
| Erythritol tetraglycidyl ether | 1 | H | H | —$CH_2$—O—$CH_2$—◁O |
| Arabinose tetraglycidyl ether | 1 | —C(=O)—H | H | —$CH_2$—O—$CH_2$—◁O |
| Triglycerol pentaglycidyl ether | 3 | H | H | H |
| Fructose pentaglycidyl ether | 1 | —C(=O)—$CH_2$—O—$CH_2$—◁O | H | —$CH_2$—O—$CH_2$—◁O |
| Xylitol pentaglycidyl ether | 1 | —$CH_2$—O—$CH_2$—◁O | H | —$CH_2$—O—$CH_2$—◁O |

TABLE 1-continued

| Compound | n | R¹ | R² | R³ |
|---|---|---|---|---|
| Tetraglycerol hexaglycidyl ether | 4 | H | H | H |
| Sorbitol hexaglycidyl ether | 1 |  | H | —CH$_2$—O—CH$_2$—\<epoxide\> |

The heterocyclic compound as another starting material for the tertiary compound of the invention is also not limited particularly and may for example be those represented by Formula (II):

(II)

wherein:
R⁴ is a hydrocarbon represented by $C_2$-$C_8$, which optionally has unsaturated bonds, is optionally substituted by a nitrogen atom, an oxygen atom or a sulfur atom, and forms a 5-membered ring, a 6-membered ring, or a 5-membered ring and a 6-membered ring.

A preferred heterocyclic compound represented by Formula (II) shown above may for example be pyrazole, benzimidazole, 1,2,4-triazole, benzotriazole, pyrrolidine, piperidine, morpholine, thiomorpholine and the like. Such a heterocyclic group may have a substituent including an alkyl group such as a methyl group, an ethyl group and the like, a hydroxy group such as a hydroxyl group, a hydroxymethyl group, a hydroxyethyl group and the like, a carbonyl group such as a formyl group, a carboxyl group and the like.

In order to obtain the tertiary compound of the invention by reacting the aforementioned heterocyclic compound with the epoxy group of the glycidyl ether group of the compound having 3 or more glycidyl ether groups, it is important that the reaction be conducted at room temperature or below, for example under a cooling condition at −78 to 25° C. Typically, the cooling to 0 to 10° C. is ensured upon adding the heterocyclic compound to the compound having 3 or more glycidyl ether groups, and after completion of the addition the temperature is raised to room temperature to ensure no remaining unreacted epoxy groups; this is not a condition for polymerization of the glycidyl ether itself.

The tertiary compound of the invention thus obtained is not limited particularly and may for example be a tertiary amine compound represented by Formula (III):

(III)

wherein:
R¹ is a hydrogen atom, a formyl group or one or two glycidyl ether groups optionally containing a carbonyl group constituted by $C_4$-$C_8$ and $O_2$-$O_4$, preferably a hydrogen atom or a glycidyl ether group;
R² is a hydrogen atom, a methyl group or an ethyl group, preferably a hydrogen atom or an ethyl group;
R³ is a hydrogen atom, a formyl group or one or two glycidyl ether groups optionally containing a carbonyl group constituted by $C_4$-$C_8$ and $O_2$-$O_4$, preferably a hydrogen atom or a glycidyl ether group;
R⁴ is a hydrocarbon represented by $C_2$-$C_8$, which optionally has unsaturated bonds, is optionally substituted by a nitrogen atom, an oxygen atom or a sulfur atom, and forms a 5-membered ring, a 6-membered ring, or a 5-membered ring and a 6-membered ring; and,
n is an integer of 1 to 4.

Such a tertiary compound of the invention can be identified for example by an infrared (IR) spectroscopic measurement, and can typically be identified by observing a peak near 3400 cm$^{-1}$ assigned to the hydroxy group of the tertiary compound and a peak near 1300 cm$^{-1}$ assigned to the tertiary amine compound. The followings are the structures of the compounds belong to the tertiary compound of the invention which were obtained actually by the inventors together with the peak positions obtained by the IR spectrometry.

(IIIa)

IR: 3400, 2910, 1450, 1310, 1290, 1110 (cm$^{-1}$)

(IIIb)

IR: 3400, 2920, 1440, 1310, 1280, 1110 (cm$^{-1}$)

(IIIc)

IR: 3410, 2910, 1450, 1300, 1280, 1110 (cm⁻¹)

(IIId)

IR: 3400, 2910, 1440, 1310, 1280, 1110 (cm⁻¹)

(IIIe)

IR: 3400, 2910, 1460, 1320, 1270, 1110 (cm⁻¹)

(IIIf)

IR: 3400, 2920, 1440, 1310, 1280, 1110 (cm⁻¹)

(IIIg)

IR: 3410, 2920, 1440, 1320, 1270, 1090 (cm⁻¹)

(IIIh)

IR: 3400, 2920, 1430, 1320, 1280, 1100 (cm⁻¹)

(IIIi)

IR: 3400, 2930, 1450, 1320, 1280, 1110 (cm⁻¹)

(IIIj)

IR: 3410, 2920, 1440, 1320, 1270, 1100 (cm$^{-1}$)

The aforementioned tertiary compound of the invention can be quaternarized to form a quaternary ammonium compound (hereinafter referred to as "a quaternary compound of the invention"). The quaternarization of the tertiary compound can be achieved for example by a reaction of a quaternarizing agent such as a halogenated alkyl, halogenated alkenyl or halogenated aryl, dialkyl sulfate and the like with a tertiary compound of the invention. This quaternarization reaction is conducted preferably under reflux or cooling condition. Typically, the reaction with a halogenated substance is subjected for example to a condition involving a reflux using an aprotic solvent acetone or acetonitrile as a reaction solvent, while the reaction with the dialkyl sulfate is subjected for example to a condition involving a cooling to 0 to 10° C. using acetone or acetonitrile or water as a reaction solvent.

The quaternary compound of the invention thus obtained is not limited particularly and may for example be a quaternary ammonium compound represented by Formula (IV) (hereinafter referred to simply as "Compound (IV)"):

(IV)

wherein:

$R^1$ is a hydrogen atom, a formyl group or one or two glycidyl ether groups optionally containing a carbonyl group constituted by $C_4$-$C_8$ and $O_2$-$O_4$, preferably a hydrogen atom or a glycidyl ether group;

$R^2$ is a hydrogen atom, a methyl group or an ethyl group, preferably a hydrogen atom or an ethyl group;

$R^3$ is a hydrogen atom, a formyl group or one or two glycidyl ether groups optionally containing a carbonyl group constituted by $C_4$-$C_8$ and $O_2$-$O_4$, preferably a hydrogen atom or a glycidyl ether group;

$R^4$ is a hydrocarbon represented by $C_2$-$C_8$, which optionally has unsaturated bonds, is optionally substituted by a nitrogen atom, an oxygen atom or a sulfur atom, and forms a 5-membered ring, a 6-membered ring, or a 5-membered ring and a 6-membered ring;

$R^5$ is a hydrocarbon optionally having unsaturated bonds represented by $C_1$-$C_7$, preferably a $C_1$-$C_3$ hydrocarbon;

X is a halogen atom or a monoalkyl sulfate represented by $C_1$-$C_7$, preferably a halogen atom selected from a chlorine atom, bromine atom or iodine atom, or a monoalkyl sulfate represented by $C_1$-$C_3$; and, n is an integer of 1 to 4.

The counter anion (X$^-$) of the aforementioned compound (IV) is not limited to those described above and may for example be a hydroxide ion derived from the counter anion. Such a hydroxide ion derived from the counter anion can be obtained by treating the compound (IV) for example with an anion exchange resin according to a standard method.

Such a quaternary compound of the invention can be identified for example by an infrared (IR) spectroscopic measurement, and can typically be identified by observing a peak near 1700 cm$^{-1}$ assigned to the quaternary ammonium compound and a loss of the peak near 1300 cm$^{-1}$ assigned to the tertiary amine compound. The followings are the structures of the compounds belong to the quaternary compound of the invention which were obtained actually by the inventors together with the peak positions obtained by the IR spectrometry.

(IVa)

IR: 3420, 2950, 1680, 1450, 1110 (cm$^{-1}$)

(IVb)

IR: 3400, 2940, 1640, 1440, 1110, 1050, 950 (cm$^{-1}$)

(IVc)

IR: 3410, 2940, 1440, 1680, 1100 (cm$^{-1}$)

(IVd)

IR: 3400, 2950, 1640, 1430, 1100, 1040, 940 (cm$^{-1}$)

(IVe)

IR: 3410, 2920, 1650, 1440, 1100 (cm$^{-1}$)

(IVf)

IR: 3420, 2930, 1630, 1450, 1100, 1050, 940 (cm$^{-1}$)

(IVg)

IR: 3400, 2920, 1640, 1450, 1110 (cm$^{-1}$)

(IVh)

IR: 3400, 2940, 1650, 1440, 1100, 1050, 960 (cm$^{-1}$)

(IVi)

IR: 3420, 2950, 1650, 1440, 1110 (cm$^{-1}$)

(IVj)

IR: 3400, 2940, 1650, 1450, 1110, 1040, 950 (cm$^{-1}$)

(IVk)

IR: 3400, 2950, 1680, 1450, 1100 (cm⁻¹)

(IVl)

IR: 3400, 2950, 1640, 1430, 1100, 1050, 950 (cm⁻¹)

(IVm)

IR: 3410, 2960, 1660, 1440, 1100 (cm⁻¹)

(IVn)

IR: 3410, 2940, 1640, 1440, 1110, 1040, 960 (cm⁻¹)

(IVo)

IR: 3400, 2950, 1680, 1440, 1100 (cm⁻¹)

(IVp)

IR: 3400, 2940, 1640, 1450, 1100, 1040, 960 (cm⁻¹)

(IVq)

IR: 3420, 2960, 1680, 1440, 1110 (cm$^{-1}$)

(IVr)

IR: 3400, 2950, 1630, 1460, 1110, 1050, 950 (cm$^{-1}$)

(IVs)

IR: 3420, 2950, 1670, 1430, 1100 (cm$^{-1}$)

(IVt)

IR: 3400, 2950, 1640, 1440, 1110, 1040, 950 (cm$^{1}$)

While any of the aforementioned tertiary compound and quaternary compound of the invention can be employed in various applications alone or in combination, it can be employed for example as a copper plating bath additive. In such a case, the concentration of such a compound in the copper plating bath is 0.1 to 1000 mg/L, preferably 1 to 800 mg/L.

The copper plating bath to which the copper plating bath additive is added is not limited particularly, and may for example be those containing copper ions and organic acids or inorganic acids.

The copper ion source capable of being contained in such a copper plating bath may be any of the copper compounds employed in an ordinary copper plating bath without any limitation. Those exemplified typically are copper sulfates, copper oxides, copper chlorides, copper carbonates, copper pyrophosphate, as well as copper alkane sulfonates such as copper methanesulfonate and copper propanesulfonate, copper alkanolsulfonates such as copper isethionate and copper propanolsulfonate, organic acid copper such as copper acetate, copper citrate and copper tartarate as well as the salts thereof. Any of these copper compounds can be employed alone or in combination.

The concentration of the copper ion in the composition of a copper plating bath is 10 to 80 g/L, preferably 35 to 75 g/L.

On the other hand, the organic acid or the inorganic acid capable of being contained in the copper plating bath is not limited particularly and any of those capable of dissolving the copper can be employed. Those preferred typically are sulfuric acid, alkane sulfonic acids such as methanesulfonic acid and propanesulfonic acid, alkanol sulfonic acids such as isethionic acid and propanolsulfonic acid, organic acids such as citric acid, tartaric acid and formic acid. Any of these organic acids or inorganic acids can be employed alone or in combination. The copper plating bath is kept preferably acidic. The concentration of this organic acid or inorganic acid is 5 to 200 g/L, preferably 10 to 100 g/L in the composition of the copper plating bath.

While this copper plating bath contains a metal copper as its primary constituent, it may contain other metals such as Ge, Fe, In, Mn, Mo, Ni, Co, Pb, Pd, Pt, Re, S, Ti, W, Cd, Cr, Zn, Sn, Ag, As, Au, Bi, Rh, Ru, Ir and the like.

Also to this copper plating bath, a halogen ion such as chloride, iodide and bromide ions can be added similarly to an ordinary acidic copper plating bath. In such a case, the concentration of the halogen ion is 0.01 to 150 mg/L, preferably 10 to 100 mg/L in the composition of the copper plating bath.

Moreover, the aforementioned copper plating bath may contain one or more of sulfoalkylsulfonic acids and the salts thereof, bissulfo-organic compounds and dithiocarbamic acid derivatives. These are the additive components also referred to generally as carrier components or brighteners, and those exemplified typically are the following (1) to (3).

(1) A sulfoalkylsulfonic acid represented by Formula (a):

wherein $L_1$ is a $C_1$-$C_{18}$ saturated or unsaturated alkylene group and $M_1$ is a hydrogen or an alkaline metal.

(2) A bissulfo-organic compound represented by Formula (b):

wherein $X_1$ and $Y_1$ are sulfate residues or phosphate residues and $L_2$ and $L_3$ are $C_1$-$C_{18}$ saturated or unsaturated alkylene groups.

(3) A dithiocarbamic acid derivative represented by Formula (c):

wherein each of R6 and R7 is a hydrogen atom or a C1-C3 lower alkyl group, L4 is a C3-C6 alkylene group and X2 is a sulfate residue or a phosphate residue.

The aforementioned components may be employed alone or in combination. The concentration is 0.1 to 200 mg/L, preferably 0.3 to 20 mg/L in the composition of the copper plating bath.

In addition to the aforementioned components, the copper plating may contain other components employed generally in the copper plating, including polyethers, such as polyethylene glycol and polypropylene glycol, Pluronic type surfactants, Tetronic type surfactants, polymers such as polyethylene glycol glyceryl ether and polyethylene glycol dialkyl ethers and humectants for reducing the surface tension, so-called levellers such as polyalkyleneimines, alkylimidazoline compounds, auramine and derivative thereof, organic dyes such as phthalocyanine compounds and janus green and the like.

The aforementioned copper plating bath may be prepared by a standard method, the details of which may be determined appropriately by taking respective component compositions and contents into consideration.

Next, the copper plating method using the copper plating bath of the present invention is described.

The substrate subjected to the copper plating method of the invention is not limited particularly, and may be a substrate made for example from a resin on which a layer of a conductive material such as a metal is formed and patterned, a semiconductor substrate such as a silicon wafer having a fine circuit pattern on the surface thereof, an electronic circuit board such as a print circuit board and the like.

Such a substrate may contain a mixture of a blind via hole, a trench (groove) for a fine circuit, a through hole penetrating the substrate and the like.

Typically, such a substrate may for example be a print board such as a package board to which an IC bare chip is mounted directly, a silicon wafer to which an LSI or the like is mounted directly, or a silicon wafer substrate for the purpose of manufacturing a semiconductor chip itself.

In order to practice the copper plating method of the invention, a pretreatment such as formation of a barrier layer is performed if necessary, and then a conductivity imparting treatment such as formation of a metal seed layer serving as a power supply layer for the substrate is performed. This conductivity imparting treatment can be accomplished by an ordinary conductivity imparting treatment method such as a metal (including carbon) coating treatment using a electroless plating, a so-called direct plating treatment method using a carbon or palladium, a sputtering, a vapor deposition or a chemical vapor deposition (CVD) and the like.

Following the conductivity imparting treatment, the substrate is subjected to a copper plating in a copper plating bath. The condition under which the copper plating is performed using the copper plating bath of the invention is not limited particularly, and any ordinary copper sulfate plating condition may be adopted. Thus, the plating may be effected at a fluid temperature of about 20 to 30° C., a cathode current density of about 0.05 to 3 A/dm². The plating time period may be adjusted appropriately in view of the purpose of the plating. Also upon this plating, it is preferable to effect a fluid agitation for example by an aeration, a pump circulation, a paddle stirring and the like.

The copper plating method described above allows a blind via hole, a through hole, a trench, a through-silicon electrode on the aforementioned substrate to be filled in a state where the superficial layer plating thickness (the thickness of the portion of the substrate which can be plated simultaneously with, but is free of the blind via hole, the through hole, the trench, the through-silicon electrode) is thin.

Typically, for copper plating of a patterned board having a blind via hole of 50 μm in diameter and 30 μm in depth to allow the via hole to be filled completely, the plating may be effected for about 30 minutes at a cathode current density of 1.5 A/dm². In such a case, the superficial layer plating thickness becomes about 10 μm.

For copper plating of a substrate such as a silicon wafer having a via hole or a trench of 0.1 to 0.5 μm in diameter and 0.2 to 1 μm in depth to allow the via hole or the trench to be filled completely for the purpose of manufacturing a semiconductor, the plating may be effected for about 150 seconds at a cathode current density of 2 A/dm². In such a case, the superficial layer plating thickness becomes about 1 μm.

In a case of the filling plating of a through-silicon electrode of 10 μm in diameter and 20 μm in depth for the purpose of a tridimensional mounting, the plating may be effected for about 10 minutes at a cathode current density of 2 A/dm². In such a case, the superficial layer plating thickness becomes about 5 μm. Also in a case of the filling plating of a through-silicon electrode of 20 μm in diameter and 100 μm in depth, the plating may be effected for about 60 minutes at a cathode current density of 0.2 A/dm². In such a case, the superficial layer plating thickness becomes about 3 μm.

The plating methods of the present invention described above can be applied to various plating procedures or devices with no limitation.

EXAMPLES

The present invention is further described in detail with referring to Examples, to which the invention is not limited in any way.

Example 1

Synthesis of Tertiary Amine Compound (IIIa):

A reaction container fitted with a thermometer, a stirrer and a drip funnel was charged with 20 g of glycerin triglycidyl ether (epoxy equivalent: 143 g/e.q.) and then also with 100 mL of pure water for dissolution, which was cooled to 0° C. and then treated with 10.2 g of pyrrolidine slowly so that the reaction temperature was kept at 30° C. or below. Thereafter, the temperature was raised to room temperature and the reaction was continued for 2 hours, after which the disappearance of the signals assigned to the epoxide (2.54, 2.71, 3.08 ppm) was confirmed by NMR. Concentration under reduced pressure for removing the reaction solvent and the excessive pyrrolidine yielded 29.9 g of a tertiary amine compound.

The functional groups of the resultant tertiary amine compound were verified by IR measurement, which showed the peaks at 3400, 2910, 1450, 1310, 1290 and 1110 cm$^{-1}$, which were confirmed to include the peak assigned to the hydroxy group (3400 cm$^{-1}$) and the peaks assigned to the tertiary amine compound (1310, 1290 cm$^{-1}$).

Based on these results, it was proven that the tertiary amine compound (IIIa) was obtained.

Example 2

Synthesis of Quaternary Ammonium Compound (IVa):

A reaction container fitted with a thermometer, a stirrer, a drip funnel and a Dimroth condenser was charged with 29.9 g of the tertiary amine compound (IIIa) obtained in Example 1 described above, and then also with 100 mL of acetonitrile for complete dissolution, and charged further with 17.4 mL of methyl iodide, and reaction was conducted by heating under reflux for 12 hours. Then the reaction solvent and the excessive methyl iodide were removed by concentration under reduced pressure, thereby yielding a quaternary ammonium compound.

The functional groups of the resultant quaternary compound were verified by IR measurement, which indicated that the peaks assigned to the tertiary amine compound (1310, 1290 cm$^{-1}$) had disappeared and the peaks assigned to the quaternary ammonium compound (1680 cm$^{-1}$) was newly observed.

Based on these results, it was proven that the quaternary ammonium compound (IVa) was obtained.

Example 3

Synthesis of Tertiary Amine Compound (IIIj):

According to Example 1, 20 g of sorbitol hexaglycidyl ether (epoxy equivalent: 170 g/e.q.) and 10.4 g of piperidine were reacted and the disappearance of the signals assigned to the epoxide (2.54, 2.71, 3.08 ppm) was confirmed by NMR, thereby obtaining 30.0 g of a tertiary amine compound.

The functional groups of the resultant tertiary compound were verified by IR measurement, which showed the peaks at 3410, 2920, 1440, 1320, 1270 and 1100 cm$^{-1}$, which were confirmed to include the peak assigned to the hydroxy group (3410 cm$^{-1}$) and the peaks assigned to the tertiary amine compound (1320, 1270 cm$^{-1}$).

Based on these results, it was proven that the tertiary amine compound (IIIj) was obtained.

Example 4

Synthesis of Quaternary Ammonium Compound (IVt):

According to Example 2, 30.0 g of the tertiary amine compound (IIIj) obtained in Example 3 described above and 19.2 mL of allyl chloride were reacted to obtain 39.0 g of a quaternary ammonium compound.

The functional groups of the resultant quaternary ammonium compound were verified by IR measurement, which indicated that the peaks assigned to the tertiary amine compound (1320, 1270 cm$^{-1}$) had disappeared and the peaks assigned to the quaternary ammonium compound (1640 cm$^{-1}$) and the peaks assigned to the allyl group (1040, 950 cm$^{-1}$) were newly observed.

Based on these results, it was proven that the quaternary ammonium compound (IVt) was obtained.

Example 5

Copper Plating onto Resin Board

An epoxy resin board having a seed layer formed by an electroless copper plating and a blind via hole of 70 μm in diameter and 40 μm in depth (aspect ratio: 0.57) was subjected to copper electroplating using the copper plating bath having the composition shown below containing the tertiary amine compound (IIIa) synthesized in Example 1 under the condition shown below.

(Copper Plating Bath Composition)
Copper sulfate pentahydrate: 230 g/L
Sulfuric acid (98%): 50 g/L
Chlorine: 40 mg/L
Tertiary amine compound (IIIa): 100 mg/L
SPS (*): 1 mg/L
* Bis 3-(sulfopropyl)disulfide
(Copper Electroplating Condition)
Plating temperature: 25° C.
Cathode current density: 2 A/dm²
Plating time: 35 minutes
Stirring: Air stirring

Example 6

Copper Plating onto Resin Board

An epoxy resin board having a seed layer formed by an electroless copper plating and a blind via hole of 70 μm in diameter and 40 μm in depth (aspect ratio: 0.57) was subjected to copper electroplating using the copper plating bath having the composition shown below containing the quaternary ammonium compound (IVa) synthesized in Example 2 under the condition shown below.

(Copper Plating Bath Composition)
Copper sulfate pentahydrate: 230 g/L
Sulfuric acid (98%): 50 g/L
Chlorine: 40 mg/L
Quaternary ammonium compound (IVa): 100 mg/L
SPS (*): 1 mg/L
* Bis 3-(sulfopropyl)disulfide
(Copper Electroplating Condition)
Plating temperature: 25° C.
Cathode current density: 2 A/dm$^2$
Plating time: 25 minutes or 35 minutes
Stirring: Air stirring

Comparative Example 1

Copper Plating onto Resin Board (1):

A resin board was subjected to copper electroplating in the same manner as Example 5 except that 4 mg/L of Janus Green B and 100 mg/L of PEG4000 were used in place of 100 mg/L of the tertiary amine compound (IIIa) in the copper plating bath.

Comparative Example 2

Copper Plating onto Resin Board (2):

A resin board was subjected to copper electroplating in the same manner as Example 5 except that 100 mg/L of the quaternary ammonium compound constituted by polyethylene glycol (nano-polymer), dimethylamine and allyl chloride represented by the formula shown below was used in place of 100 mg/L of the tertiary amine compound (IIIa) in the copper plating bath.

Test Example 1

Figure 1:
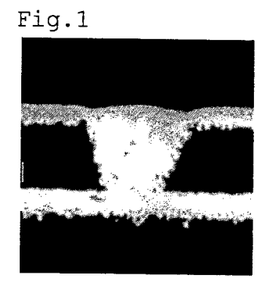
FIG. 1 shows a photograph as a sectional view of the inside of the via hole after plating in Example 5.
Figure 2:
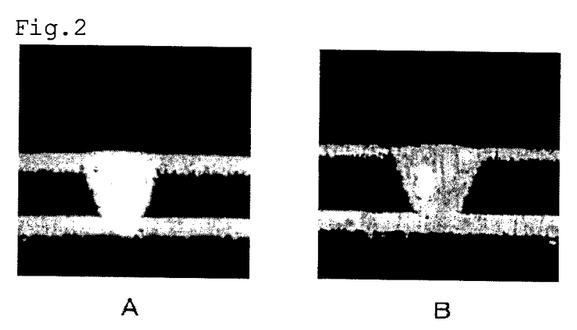
FIG. 2 shows photographs as sectional views of the inside of the via hole after plating in Example 6 (plating time: 35 minutes in A, and 25 minutes in B).
Figure 3:
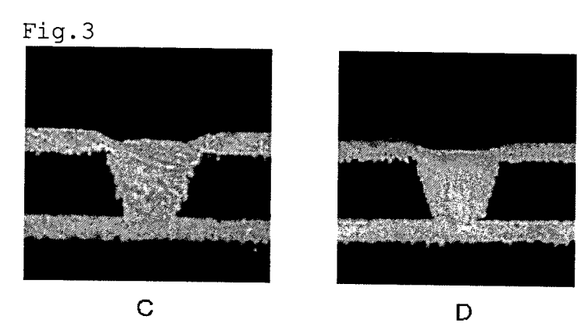
FIG. 3 shows a photograph as a sectional view of the inside of the via hole after plating in Comparative 1 or 2 (C in Comparative 1 and D in Comparative 2).

Evaluation of Copper Plating:

FIG. 1 shows a photograph as a sectional view of the resin board which has been subjected to the copper electroplating in Example 5 (plating time: 35 minutes) and FIG. 2 shows photographs as sectional views of the resin board which has been subjected to the copper electroplating in Example 6 (plating time: 35 minutes in A and 25 minutes in B). FIG. 3 also shows a photograph as a sectional view of the resin board which has been subjected to the copper electroplating in Comparative Example 1 or 2 (C in Comparative 1 and D in Comparative 2, plating time: 35 minutes in both cases).

Example 5 and Example 6 exhibited satisfactory filling performances when compared with Comparative Examples 1 or 2. Especially as shown in B of FIG. 2, Example 6 allowed for a complete via filling within 25 minutes of the plating time period, indicating that the filling was possible with a plating thickness as extremely thin as a superficial layer plating thickness of 9.1 μm. Accordingly, it was indicated that the present invention can be applied to a fine pattern circuit.

Example 7

Copper Plating onto Silicon Wafer Board:

A silicon wafer board having a Cu seed layer formed by a vacuum sputtering and a blind via hole of 20 μm in diameter and 110 μm in depth (aspect ratio: 5.5) was subjected to copper electroplating using the copper plating bath having the composition shown below containing the tertiary amine compound (IIIj) synthesized in Example 3 under the condition shown below.

Figure 4:
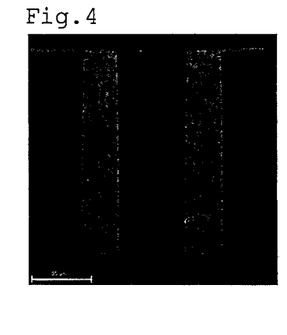
FIG. 4 shows a photograph as a sectional view of the inside of the via hole after plating in Example 7.

(Copper Plating Bath Composition)
Copper sulfate pentahydrate: 250 g/L
Sulfuric acid (98%): 30 g/L
Chlorine: 40 mg/L
Tertiary amine compound (IIIj): 10 mg/L
SPS (*): 1 mg/L
* Bis 3-(sulfopropyl)disulfide
(Copper Electroplating Condition)
Plating temperature: 25° C.
Cathode current density: 0.4 A/dm$^2$
Plating time: 80 minutes
Stirring: Squeeze stirring FIG. 4 shows a photograph as a sectional view of the silicon wafer board which has been subjected to the copper electroplating. Based on this figure, it was indicated that the present invention exerted a satisfactory filling performance even for the silicon wafer board.

As discussed above, while a conventional plating bath for a via filling has a difficulty in a bottom-up filling when the aspect ratio is 1 or more which leads to a void in a via hole, the present invention allows for a filling without any void in plating a via hole even when aspect ratio is more than 2.

INDUSTRIAL APPLICABILITY

The novel compounds of the present invention can be utilized in an additive for a copper plating bath. The copper plating bath containing this novel compound is preferable especially for plating a substrate.

The invention claimed is:

1. A copper plating bath, comprising:
    copper ion at 10 to 80 g/L,
    an organic acid or an inorganic acid at 5 to 200 g/L, and
    one or more compounds selected from the group consisting of a tertiary amine compound obtained by reacting a heterocyclic compound with an epoxy group of a glycidyl ether group of a compound having 3 or more glycidyl ether groups at room temperature or below without polymerizing the glycidyl ether groups and a quaternary ammonium compound obtained by quaternarizing the tertiary amine compound, wherein
the heterocyclic compound is represented by Formula (II):

(II)

wherein:
R$^4$ is a hydrocarbon represented by C$_2$-C$_8$, which optionally has unsaturated bonds, is optionally substituted by a nitrogen atom, an oxygen atom or a sulfur atom, and forms a 5-membered ring, a 6-membered ring, or a 5-membered ring and a 6-membered ring, and
the compound having 3 or more glycidyl ether groups is represented by Formula (I):

(I)

wherein:
R$^1$ is a hydrogen atom, a formyl group or one or two glycidyl ether groups optionally containing a carbonyl group constituted by C$_4$-C$_8$ and O$_2$-O$_4$;
R$^2$ is a hydrogen atom, a methyl group or an ethyl group;
R$^3$ is a hydrogen atom, a formyl group or one or two glycidyl ether groups optionally containing a carbonyl group constituted by C$_4$-C$_8$ and O$_2$-O$_4$; and,
n is an integer of 1 to 4.

2. The copper plating bath according to claim 1, wherein the copper plating bath comprises said copper ion at 35 to 75 g/L and said organic acid or inorganic acid at 10 to 100 g/L.

3. The copper plating bath according to claim 1, wherein the copper plating bath comprises one or more compounds selected from the group consisting of the tertiary amine compound and a quaternary ammonium compound obtained by quaternarizing the tertiary amine compound at 0.1 to 1000 mg/L.

4. The copper plating bath according to claim 1, wherein the copper plating bath further comprises one or more components selected from the group consisting of sulfoalkylsulfonic acids or salts thereof, bissulfo-organic compounds and dithiocarbamic acid derivatives and the concentration of said components is 0.1 to 200 mg/L.

5. The copper plating bath according to claim 1, wherein the copper plating bath is acidic.

6. A copper plating method, comprising:
plating a substrate by contacting said substrate with the copper plating bath according to claim 1.

7. The copper plating method according to claim 6, wherein the substrate has a blind via hole whose aspect ratio is 1 or more.

8. The copper plating method according to claim 6, wherein the substrate has a through hole whose aspect ratio is 2 or more.

9. The copper plating method according to Claim 6, which is conducted so that a superficial layer plating thickness is 15 µm or less.

10. The copper plating bath according to claim 1, wherein tertiary amine compound is represented by Formula (III):

(III)

wherein:
R$^1$ is a hydrogen atom, a formyl group or one or two glycidyl ether groups optionally containing a carbonyl group constituted by C$_4$-C$_8$ and O$_2$-O$_4$;
R$^2$ is a hydrogen atom, a methyl group or an ethyl group;
R$^3$ is a hydrogen atom, a formyl group or one or two glycidyl ether groups optionally containing a carbonyl group constituted by C$_4$-C$_8$ and O$_2$-O$_4$;
R$^4$ is a 5-membered ring or a 6-membered ring, optionally having unsaturated bonds and optionally substituted by a nitrogen atom, an oxygen atom or a sulfur atom, which is represented by C$_2$-C$_8$ or a hydrocarbon forming the 5-membered ring and the 6-membered ring; and,
n is an integer of 1 to 4.

11. The copper plating bath according to claim 1, comprising one or more of said tertiary amine compounds.

12. The copper plating bath according to claim 1, comprising one or more of said quaternary ammonium compounds.

13. The copper plating bath according to claim 10, comprising one or more of said tertiary amine compounds.

14. The copper plating bath according to claim 10, comprising one or more of said quaternary ammonium compounds.

15. The copper plating bath according to claim 1, wherein R$^4$ is a hydrocarbon represented by C$_2$-C$_8$, which optionally has unsaturated bonds, is optionally substituted by a nitrogen atom, an oxygen atom or a sulfur atom, and forms a 5-membered ring or a 6-membered ring.

* * * * *